US011224613B2

(12) United States Patent
Konkol et al.

(10) Patent No.: US 11,224,613 B2
(45) Date of Patent: Jan. 18, 2022

(54) LIGNEOUS PLANT-DERIVED HETEROPOLYSACCHARIDES FOR USE IN TREATMENT OF UROLOGIC SYMPTOMS AND DISEASES

(71) Applicant: MONTINUTRA LTD, Raisio (FI)

(72) Inventors: Yvonne Konkol, Turku (FI); Jenni Bernoulli, Turku (FI); Bjarne Holmbom, Turku (FI); Heikki Vuorikoski, Paimio (FI); Andrey Pranovich, Turku (FI); Jussi Halleen, Kiviniemi (FI)

(73) Assignee: MONTINUTRA LTD, Raisio (FI)

( * ) Notice: Subject to any disclaimer, the term of this patent is extended or adjusted under 35 U.S.C. 154(b) by 0 days.

(21) Appl. No.: 15/697,568

(22) Filed: Sep. 7, 2017

(65) Prior Publication Data

US 2018/0008627 A1 Jan. 11, 2018

Related U.S. Application Data

(62) Division of application No. 14/441,933, filed as application No. PCT/FI2013/051057 on Nov. 8, 2013, now abandoned.

(30) Foreign Application Priority Data

Nov. 9, 2012 (FI) .................................... 20126175

(51) Int. Cl.
| | |
|---|---|
| *A61K 31/736* | (2006.01) |
| *A23L 33/24* | (2016.01) |
| *A61K 36/15* | (2006.01) |
| *A23K 20/163* | (2016.01) |

(52) U.S. Cl.
CPC .......... *A61K 31/736* (2013.01); *A23K 20/163* (2016.05); *A23L 33/24* (2016.08); *A61K 36/15* (2013.01); *A23V 2002/00* (2013.01)

(58) Field of Classification Search
CPC .... A61K 31/736; A61K 36/15; A23K 20/163; A23L 33/24; A23V 2002/00
USPC ......................................................... 514/54
See application file for complete search history.

(56) References Cited

U.S. PATENT DOCUMENTS

| | | | |
|---|---|---|---|
| 2005/0203291 A1* | 9/2005 | Svenson .................. | C07H 1/08 536/124 |
| 2011/0172181 A1 | 7/2011 | Danhof | |

FOREIGN PATENT DOCUMENTS

| | | |
|---|---|---|
| EP | 0 400 586 | 12/1990 |

OTHER PUBLICATIONS

Xu et al. (Cellulose Chem. Technol., 41(1),51-62 (2007)).*
Lundqvist et al. (Carbohydrate Polymers 51 (2003) 200-211).*
Goebbels et al. (Appl Pathol. 1985;3(4):242-54) (abstract sent).*
Spiess et al. (Urologic Oncology: Seminars and Original Investigations 25 (2007) 38-45). (Year: 2007).*
Lewis (Radiology vol. 162, No. 2, Published Online: Feb. 1, 1987) (abstract sent).*
Zukerberg et al. (Human Pathology, vol. 21, Issue 9, Sep. 1990, pp. 932-935).*
Kelly, "Larch Arabinogalactan: Clinical Relevance of a Novel Immune-Enhancing Polysaccharide" *Alternative Medicine Review*, vol. 4, No. 2: pp. 96-103 (1999).
Medvedeva et al. "Preparation of high-purity larch arabinogalactan and study of immunomodulatory effects thereof" *Chemistry of herbal substances*, No. 4: pp. 17-23 (2004).
Translation of Russian Office Action issued in Appln. No. 2015122037/10(034274) dated Nov. 9, 2017.
Translation of Japanese Office Action issued in Appln. No. 2015-541201 dated Sep. 15, 2017.
Written Opinion of the International Searching Authority, for International Application No. PCT/FI2013/051057, dated May 9, 2015.
Bulletin of Applied Glycoscience, 2012, vol. 2, No. 3, pp. 180-184.
Ebringerová et al., "Norway spruce galactoglucomannans exhibiting immunomodulating and radical-scavenging activities" *International Journal of Biological Macromolecules* vol. 42 pp. 1-5 (2008).
Ghoneum, et al., "Immunomodulatory and anticancer effects of active hemicellulose compound (AHCC)" Int. J. Immunotherarpy XI(I): pp. 23-28 (1995).
Hashi et al., "Antitumor Effect of 4-O-Methylglucuronoxylan on Solid Tumor in Mice" *Agric. Biol. Chem.*, vol. 43, No. 5: pp. 951-959 (1979).
Hashi, "Antitumor Effects and Anti-complementary Effects of Tree Polysaccharides" *Bull. For. & For. Prod. Res. Inst.*, No. 360, pp. 121-148 (1991) with English Summary.
Hsieh et al., "Changes in Cell Growth, Cyclin/Kinase, Endogenous Phosphoproteins and nm 23 Gene Expression in Human Postatic JCA-1 Cells Treated with Modified Citrus Pectin" *Biochemistry and Molecular Biology International*, vol. 37, No. 5: pp. 833-841 (Nov. 1995).
Leppänen et al., "Pressurized hot water extraction of Norway spruce hemicelluloses using a flow-through system" *Wood Sci Technol*, No. 45: pp. 223-236 (2011).
Lundqvist et al., "Characterization of galactoglucomannan extracted from spruce (*Picea abies*) by heat-fractionation at different conditions" *Carbohydrate Polymers*, vol. 51: pp. 200-211 (2003).
Song et al., "Extraction of galactoglucomannan from spruce wood with pressurised hot water" *Holzforschung*, vol. 62, pp. 659-666 (2008).
Willför et al., "Characterisation of water-soluble galactoglucomannans from Norway spruce wood and thermomechanical pulp" *Carbohydrate Polymers*, vol. 52: pp. 175-187 (2003).

(Continued)

*Primary Examiner* — Shaojia A Jiang
*Assistant Examiner* — Michael C Henry
(74) *Attorney, Agent, or Firm* — Nixon & Vanderhye PC

(57) ABSTRACT

The present invention relates to preventing and/or treating urologic diseases and symptoms in humans or domestic animals. The present invention relates also to preventing and/or treating pain in the pelvic area. The invention relates to use of a heteropolysaccharide composition isolated from ligneous plants and comprising hemicelluloses, mainly glucomannans, but also xylans and pectic polysaccharides, as well as fractions, subgroups or mixtures of these, as pharmaceutical preparations, food additives and food products.

19 Claims, 3 Drawing Sheets

(56) References Cited

OTHER PUBLICATIONS

Xu et al., "Physico-Chemical Characterization of Spruce Galactoglucomannan Solutions: Stability, Surface Activity and Rheology" *Cellulose Chemistry and Technology*, vol. 41, No. 1: pp. 51-62 (2007).
Yin et al., "Structural characterization and anti-tumor activity of a novel heteropolysaccharide isolated from *Taxus yunnanensis*" *Carbohydrate Polymers*, vol. 82: pp. 543-548 (2010).
Office Action issued in RU Appln. No. 2015122037/10(034274) dated Jul. 16, 2018 (w/ translation).
Mizuno et al., "Anti-tumor Polysaccharide from the Mycelium of Liquid-cultured *Agaricus blazei* Mill" *Biochemistry and Molecular Biology International*, vol. 47, No. 4, Apr. 1999, pp. 707-714.
Office Action issued in EP Appln. No. 13 814 186.6 dated Mar. 8, 2019.
Yan et al., "PectaSol-C Modified Citrus Pectin Induces Apoptosis and Inhibition of Proliferation in Human and Mouse Androgen-Dependent and Independent Prostate Cancer Cells" *Integrative Cancer Therapies*, vol. 9, No. 2: 197-203 (2010).

\* cited by examiner

*) p=0.06

LIGNEOUS PLANT-DERIVED HETEROPOLYSACCHARIDES FOR USE IN TREATMENT OF UROLOGIC SYMPTOMS AND DISEASES

This application is a divisional of U.S. application Ser. No. 14/441,933, filed May 11, 2015, which is the U.S. national phase of International Application No. PCT/FI2013/051057 filed Nov. 8, 2013 which claims priority to Finnish (FI) Application No. 20126175 filed Nov. 9, 2012, the entire contents of each of which are hereby incorporated by reference.

FIELD OF THE INVENTION

The present invention provides a therapeutic agent for preventing and treating urologic diseases and symptoms in humans and domestic animals. Furthermore, the invention relates to a use of ligneous plant-derived compositions or mixtures of carbohydrates isolated therefrom as a pharmaceutical preparation, food additive and food products.

BACKGROUND OF THE INVENTION

Lower urinary tract (LUT) diseases generally mean all diseases which cause lower urinary tract symptoms and include various functional disorders and diseases of the bladder, prostate and the urethra. Diseases of the LUT are very heterogeneous and are often diagnosed as syndromes owing to varying combinations of symptoms and lack of known aetiology. Both women and men are affected by LUT symptoms. Roughly, LUT diseases can be divided into bladder- and prostate-related diseases. The most common diseases associated with LUT symptoms related to the prostate in men include prostatitis, which is an umbrella term referring to several types of prostatitis, such as chronic nonbacterial prostatitis/chronic pelvic pain syndrome (CP/CPPS), and benign prostatic hyperplasia (BPH). In women, common diseases related to the bladder include interstitial cystitis/painful bladder syndrome (IC/PBS) and urinary incontinence.

The lower urinary tract (LUT) symptoms are the subjective indicator of a disease or change in condition as perceived by the patient, carer or partner. They are usually qualitative. The LUT symptoms are roughly divided into three categories: storage symptoms, voiding symptoms, and post micturition symptoms. Increased daytime frequency, nocturia, incontinence (as several different forms) and urgency are examples of storage symptoms. Voiding symptoms are experienced during the voiding phase. Examples include intermitted stream, slow stream, splitting or spraying of the urine stream, prolonged micturition, hesitancy, straining, and terminal dribble. Feelings of incomplete bladder emptying and post micturition dribble are examples of the post micturition symptoms.

Pain is often associated with LUT symptoms and diseases. Pain in the pelvic and genitourinary area produces the greatest impact on the patient and quality of life. Based on the site of pain, the feeling of acute or chronic pain can be categorized e.g. as bladder, urethral, vulval, vaginal, scrotal, perineal, or pelvic pain. Genital and LUT pain can also be diagnosed as unspecified syndromes where the precise cause of the feeling of pain has not been defined.

In addition to LUT symptoms experienced by humans, also domestic animals such as cats and dogs suffer from LUT signs without any known causes. Such signs can be acute or chronic and result from various abnormalities within the LUT itself and the LUT function thereof. There is often inflammation in the bladder not related to bacterial infection, but there can also be LUT dysfunction without any pathological signs. Like in humans, often no specific underlying cause for the symptoms can be confirmed after standard clinical evaluation of the LUT. Therefore, these symptoms are classified as chronic idiopathic signs and are often described as feline and canine interstitial cystitis.

The aetiology of different kinds of LUT disorders is yet unknown. Even the categorization of the diseases into bladder- and prostate-related disorders is questionable. For example, some researchers have suggested that chronic nonbacterial prostatitis or chronic prostatitis/chronic pelvic pain syndrome (CP/CPPS) is a form of interstitial cystitis/bladder pain syndrome (IC/PBS). Indeed, The National Institute of Diabetes and Digestive and Kidney Diseases (NIDDK) in the USA have begun to group IC/PBS and CP/CPPS under the common term of urologic chronic pelvis pain syndromes (UCPPS). It would not be surprising if further scientific studies revealed some common aetiology and pathways of the origin and progression of the many different LUT disorders and symptoms common in both men and women.

Despite the high prevalence and incidence of different LUT diseases and symptoms, effective treatment is still lacking. For example, there are two main drugs that are prescribed for treating prostatic disorders; alpha-blockers and 5-alpha-reductase inhibitors, but neither of them has been shown to be effective and both have many unwanted side effects, such as impotence, decreased libido, depression, and dizziness. There is an urgent need for new compositions for the prevention and treatment of prostate disorders and LUT associated symptoms without the unwanted side effects. Indeed, naturally occurring compounds for treatment and prevention of LUT symptoms are being extensively studied, such as saw palmetto, pygeum, and stinging nettles. One category of naturally occurring compounds is plant-derived polysaccharides, which have been shown to exert biological activities. For example, various non-cellulosic polysaccharides (also named as hemicelluloses, or heteropolysaccharides) such as polysaccharides or polysaccharide fractions isolated from *Aloe Vera*, fenugreek, and longan have been shown to exert anti-inflammatory and immunomodulatory properties (Ebringerová et al. 2008, Int. J. Biol. Macromol. 42, 1-5).

One theory of the mechanism of action of plant polysaccharides could be prebiotic effects through the colon. Plant-derived polysaccharides are hardly absorbed through the digestive system and most probably fermented by gut microbiota to various smaller molecules, such as short-chain fatty acids, which actually have been shown in published studies to have protective effects in the gut. As to the lower urinary tract, many studies published have actually shown bladder—gut interaction: neural links between pelvic organs modulate the organs' physiological function. Indeed, the role of the colon health in lower urinary tract symptoms in general is an intriguing theory and has not yet been studied in the scientific field. In any case, existing therapeutic agents for treatment of LUT disorders exert many side effects. Thus, there in an identified need for new therapeutic compositions for the prevention and treatment of prostate disorders and LUT associated symptoms.

BRIEF DESCRIPTION OF THE INVENTION

In one aspect, the present invention provides a ligneous plant-derived composition comprising heteropolyssaccharides, for use as a medicament in the treatment of urologic symptoms or diseases in a human or animal subject. According to some specific embodiments, the composition may be provided in a form of a water-extract or an isolated carbohydrate composition.

Non-limiting examples of said urologic symptoms include lower urinary tract symptoms such as increased daytime urinary frequency, nocturia, urinary incontinence, urinary urgency, intermitted urine stream, slow urine stream, splitting or spraying of the urine stream, prolonged micturition hesitancy, straining and terminal dribble, incomplete bladder emptying, post-micturition dribble, abdominal pain, pelvic pain, genitourinary pain, bladder pain, urethral pain, vulval pain, vaginal pain, scrotal pain, and perineal pain.

According to other embodiments, the ligneous plant-derived composition may be used in the treatment of a human or animal subject suffering from a urologic disease or condition selected from the group consisting of interstitial cystitis/bladder pain syndrome, hemorrhagic cystitis, overactive bladder, chronic nonbacterial prostatitis/chronic pelvic pain syndrome, benign prostate hyperplasia, prostate cancer, bladder cancer, kidney cancer, renal cell carcinoma, urothelial cell carcinoma, and testicular cancer.

In another aspect, the present invention provides a pharmaceutical composition comprising a ligneous plant-derived composition according to any embodiment of the present invention and a pharmaceutically suitable carrier.

In further aspects, the present invention provides a food or animal feed product, and a natural product comprising a ligneous plant-derived composition according to any embodiment of the present invention.

In a still further aspect, the present invention provides a method of treating at least one urologic symptom or disease in a human or animal subject in need thereof by administering an efficient amount a ligneous plant-derived composition according to any embodiment disclosed herein to said subject.

Other aspects, specific embodiments, objects, details, and advantages of the invention are set forth in the dependent claims and will become apparent from the following drawings, detailed description and examples.

BRIEF DESCRIPTION OF THE DRAWINGS

In the following the invention will be described in greater detail by means of preferred embodiments with reference to the attached drawings, in which.

DETAILED DESCRIPTION OF THE INVENTION

Figure 1:
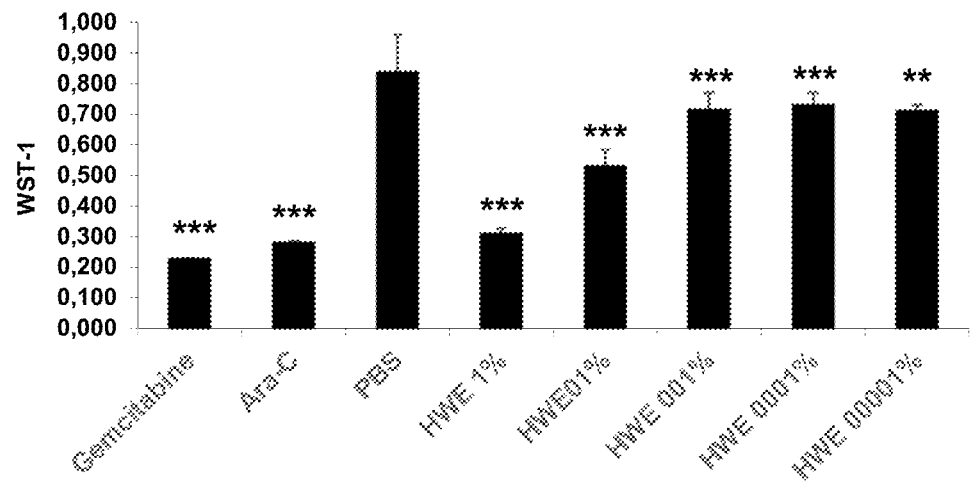
FIG. 1 shows the effect (as absorbance values) of a sof-wood hot-water extract (HWE) and two anticancerous control compounds, gemcitabine and Ara-C, on the cell proliferation of an LNCaP prostate cancer cell line. Concentrations of gemcitabine and ARA-C used were 100 nM. HWE concentrations are given as % of the final test medium volume (1% to $1 \times 10^{-4}$%, w/v).

As used herein, the term "urologic disease" refers to a wide variety of congenital or acquired dysfunctions of the urinary system. In females, urologic diseases involve the urinary tract, while in males they affect the urinary tract and/or the reproductive organs.

As used herein, the terms "lower urinary tract (LUT) symptoms" and "urologic symptoms" are interchangeable and they refer to storage symptoms, voiding symptoms, and post micturition symptoms. The LUT symptoms may or may not be associated with abdominal pain.

As used herein, the term "storage symptoms" refers to increased daytime frequency, nocturia, incontinence (as several different forms of any involuntary leakage of urine) and urgency.

As used herein, the term "voiding symptoms" refers to intermitted stream, slow stream, splitting or spaying of the urine stream, prolonged micturition hesitancy, straining and terminal dribble.

As used herein, the term "post micturition symptoms" refers to feelings of incomplete bladder emptying and post micturition dribble.

As used herein, the term "abdominal pain", whenever acute or chronic, refers to pain in the pelvic and genitourinary area including bladder, urethral, vulval, vaginal, scrotal, perineal or pelvic pain associated with or without other LUT symptoms. It refers also to genitourinary pain syndromes where varying combinations of symptoms cannot be used for precise diagnosis.

As used herein, the terms "ligneous plant" and "woody plant" are interchangeable and they refer to a plant having hard lignified tissues or woody parts, particularly stems. Non-limiting examples of ligneous plants include trees and shrubs irrespective their geographical origin.

As used herein, the term "softwood" refers to wood from gymnosperm coniferous trees such as spruce, larch and pine species.

As used herein, "hardwood" refers to wood from angiosperm decidous trees such as birch, aspen and eucalypt species.

As used herein, the term "xylans" refers to heteropolysaccharides found in ligneous plants such as hardwood and softwood, and to all xylan fractions and subgroups, such as arabinoglucuronoxylan isolated from softwood and acetyl-methylglucuronoxylan isolated from hardwood. Natural hardwood xylans exist in acetylated forms.

As used herein, the term "glucomannans" refers to heteropolysaccharides found in ligneous plants such as softwood and hardwood, and to all glucomannan fractions and subgroups, such as galactoglucomannan (GGM). Further, "glucomannans" refer to both acetylated and non-acetylated forms.

As used herein, "pectic compounds" refers to heteropolysaccharides found in ligneous plants including both softwood and hardwood such as rhamnogalacturonan, galactan and arabinan.

As used herein, the term "heteropolysaccharide" refers to a polymer of more than ten monosaccharide units, wherein two or more of the monosaccharide units are different from each other. In accordance with the definitions given above, the term includes both hemicelluloses, such as various xylans and glucomannans, and pectic compounds. The term "heterooligosaccharide" differs from the term "heteropolysaccharide" in that it contains only two to ten monosaccharide units.

As used herein, the term "ligneous plant-derived heteropolysaccharide composition" or any corresponding expression refers to a heteroplysaccharide-containing extract obtained from a stem, branch, root, tuber, or any combination thereof of a ligneous plant. Additional oligosaccharides and/or monosaccharides may or may not be present in the extracts and in isolated heteropolysaccharide preparations.

As used herein, the term "domestic animal" refers herein to cattle, pigs, horses, sheep, chickens, goats, dogs and cats regardless of breeds.

As used herein, the term "treatment" or "treating" refers not only to complete cure of LUT associated diseases or symptoms related thereto, but also to prevention, alleviation, and amelioration of said diseases or symptoms.

As used herein, the term "effective amount" refers to an amount of a ligneous plant-derived heteropolysaccharide composition in which the harmful effects of LUT symptoms and/or diseases are, at a minimum, ameliorated.

The present invention provides means and methods for treating LUT symptoms and/or LUT associated diseases in human, both male and female, or animal subjects. More specifically, said means is a ligneous plant-derived heteropolysaccharide composition. In some embodiments, the composition is in the form of a water-extract, or isolated or purified heteropolysaccharides, such as GGM, with or without additional oligosaccharides and/or monosaccharides. In further embodiments, the heteropolysaccharides are mainly in the form of glucomannans, but also as xylans and pectic polysaccharides, including fractions, subgroups or mixtures of thereof.

Polysaccharides are macromolecular/polymeric carbohydrates consisting of different monosaccharides connected to each other by glycosidic bonds. Polysaccharides, i.e. cellulose, hemicelluloses and pectins are the main constituents of wood and wood pulps. Water-soluble polysaccharides are released and accumulated into process waters in the production of mechanical pulp and wood-containing paper. Heteropolysaccharides can be extracted from wood with pressurised water at elevated temperatures in a considerable yield, 5-10% of wood. The extracted saccharides are heteropolysaccharides of several different neutral and acidic monosaccharides.

As to softwoods and hardwoods in general, the contents of the main components vary in their proportions, but polysaccharides represent the major part of both wood types. Galactoglucomannans represent the main hemicellulose component in softwoods, while xylans are the main hemicellulose component in hardwoods. Other softwood hemicelluloses are arabinogalactans, xyloglucans and other glucans, as well as pectins. The term pectin or pectic compounds is used either strictly for the component rhamnogalacturonan or more generally for the group of components comprising rhamnogalacturonans, galactans and arabinans.

The major hemicelluloses in softwoods are galactoglucomannans (GGM) and arabinoglucuronoxylans. GGM constitute the principal hemicellulose type in softwoods. The backbone of GGM is a linear chain of $\beta\text{-}(1{\rightarrow}4)$-linked D-mannopyranose and D-glucopyranose units. Galactoglucomannans can be roughly divided into two types: one with a low galactose content—referred often simply as glucomannan—and the other with a higher galactose content. Softwood arabinoglucuronoxylans and xylans of hardwood O-acetyl-4-O-methylglucurono-$\beta$-D-xylan (the main hemicellulose in hardwood), referred to as xylans for short, have both a backbone of $\beta\text{-}(1{\rightarrow}4)$-linked xylopyranose units. Both GGM in softwoods and xylans in hardwoods carry acetyl groups, about one acetyl per two monosaccharide units. The acetyl groups make these hemicelluloses soluble in water, even at room temperature.

Pectic polysaccharides such as rhamnogalacturonan has a backbone of $\alpha\text{-}(1{\rightarrow}4)$-linked D-galacturonic acid units and $\alpha\text{-}(1{\rightarrow}2)$ or $\alpha\text{-}(1{\rightarrow}4)$-linked L-rhamnose. Galactan, sometimes termed pectic galactan, has been described mainly in compression wood. This galactan has a backbone of $\beta\text{-}(1{\rightarrow}4)$-linked D-galactose units, partly substituted at the hydroxyl group of C6 with galacturonic acid units. The arabinan backbone consists of $\alpha\text{-}(1{\rightarrow}5)$-linked arabinose units with side chains of arabinose units joined by $\alpha\text{-}(1{\rightarrow}3)$ linkages.

In some non-limiting embodiments, the heteropolysaccharide-rich products for use in the present invention can be isolated by extraction of softwood or hardwood with pressurised water, such as hot water at temperatures of 160° C.-180° C., followed by precipitation with addition of ethanol to the water extracts (Song et al. 2008, Holzforschung 62, 659-666). In this way, softwoods such as spruce and pine will provide a heteropolysaccharide product with GGM as the main component, in a yield of 5-10% of the wood. The molar mass of the precipitated heteropolysaccharides is mainly in the range 4000-10000, corresponding to a degree of polymerisation of 25-60. The monosaccharide composition of this heteropolysaccharide-rich white product is typically as follows:

Galactose 8%, glucose 13%, mannose 58%, i.e. total GGM 79%;

Arabinose 2%, 4-O-methylglucuronic acid 2%, xylose 11%, i.e. total xylans 15%; and Rhamnose 1%, galacturonic acid 5%, i.e. total pectins 6%.

If desired, wood heteropolysaccharides may also be isolated and purified by precipitation in ethanol as well known to those skilled in the art.

The content of acetyl groups is typically 0.6-0.7%. The acetyl groups are substituted on the mannose units in GGM. This content of acetyl groups corresponds to a molar ratio of acetyl to mannose of 0.5, implying that every second mannose group carry an acetyl group, on average. To provide a water-soluble heteroplysaccharide product, hydrolysis of the acetyl groups must be avoided. This can be achieved by optimising the extraction temperature and time, and keeping the pH during extraction around 4.

The extraction can be performed in batch extractors or in flow-through extractors (Song et al. 2008, ibid; Leppänen et al. 2011, Wood Sci. Technol. 45(2), 223-236). Both methods give heteropolysaccharide products with a similar composition and purity. The hot-water extracts can also be purified to remove oligomeric and monomeric saccharides by membrane filtration.

Water-soluble heteropolysaccharides, still carrying most of the acetyl groups, can be recovered also from the process waters in mechanical pulp mills (Thornton et al. 1994, J. Wood Chem. Technol. 14, 159-175; Willför et al. 2003, Tappi J. 2:11, 27-32; Xu et al. 2007, Cellulol. Chem.

Technol. 51, 51-62). Precipitation with ethanol gives a heteropolysaccharide product with a very similar composition as that obtained by hot-water extraction of wood. However, the yield of GGM-rich hemicelluloses from mechanical pulping waters is rather low, only about 1% on wood basis.

In some embodiments, the heteropolysaccharide composition is a water-extract obtained from ligneous plants, such as softwood or hardwood, wherein GGMs constitute at least 50% of the total carbohydrate content of the extract. In some other embodiments, GGMs may constitute at least 80% of the total carbohydrate content in the extract, especially if ethanol precipitation is used in the production method. In some further embodiments, the extract may contain oligosaccharides with two to ten sugar units, mainly with mannose, glucose and/or galactose units, and/or monosaccharides, such as mannose, glucose, galactose, xylose and arabinose. Said oligosaccharides may be obtained and purified from wood by hydrolysis. On the other hand, if desired, the extract may be purified from said oligosaccharides and/or monosaccharides by methods known to a skilled person.

It should be understood that the term "extract" refers to a composition obtainable by extraction. Thus, the content of an extractant, i.e. an extracting agent, such as water or ethanol, may vary in said composition. In some embodiments, the extract may be provided in a dried form, such as powder.

The heteropolysaccharide compositions according to the present invention may be used to treat at least one urologic or LUT symptom in a human or animal subject including, but not limited to storage symptoms such as increased daytime urinary frequency, nocturia, urinary incontinence, involuntary urine leakage, and urinary urgency; voiding symptoms such as intermitted urine stream, slow urine stream, splitting or spraying of the urine stream, prolonged micturition hesitancy, straining and terminal dribble; post-micturition symptoms such as feelings of incomplete bladder emptying and post-micturition dribble; and abdominal pain such as acute or chronic pelvic pain, genitourinary pain, bladder pain, urethral pain, vulval pain, vaginal pain, scrotal pain, and, perineal pain. The pain symptoms may or may not be associated with the other LUT symptoms.

In addition, the present heteropolysaccharide composition may be used to treat urologic diseases such as LUT associated diseases or conditions regardless of whether the human or animal subject suffers from the LUT symptoms described above. Non-limiting examples of the LUT diseases include the following bladder and prostate diseases: urologic chronic pelvis pain syndrome (UCPPS) including interstitial cystitis/bladder pain syndrome and chronic nonbacterial prostatitis/chronic pelvic pain syndrome, hemorrhagic cystitis, overactive bladder, benign prostate hyperplasia, and prostate cancer. The heteropolysaccharide composition may also be used to treat other urologic cancers such as cancers of the bladder, kidney, and testicles. Without being limited to any hypothesis, the heteropolysaccharide composition may be especially effective in inhibiting androgen-sensitive prostate cancer cell proliferation.

In some embodiments, the urologic disease to be treated with the present heteropolysaccharide composition is not a bacterial infection, such as a urinary tract infection.

The heteropolysaccharide compositions according to various embodiments of this invention may be formulated, for instance, as pharmaceutical compositions, food or animal feed additives, food or animal feed products, natural products, or health products.

Oral administration route is the most preferable for pharmaceutical compositions which may be formulated, for example, as tablets, troches, lozenges, suspensions, dispersible powders or granules, capsules, syrups or elixirs. The required amount of the active compound may depend on the particular condition to be treated. Any kind of pharmaceutically acceptable solid or liquid carrier known to those skilled in the medicinal and pharmaceutical arts, may be used in the pharmaceutical preparation.

Amounts and regimens for the administration of the pharmaceutical compositions can be determined readily by those with ordinary skill in the clinical art of treating LUT-related symptoms and disorders. Generally, the dosage depends on considerations such as age, gender and general health of the patient to be treated; kind of concurrent treatment, if any; frequency of the treatment and nature of the effect desired; extent of tissue damage; duration of the symptoms; and other variables. A desired dose may be administered in one or more applications to obtain the desired results. If desired, the pharmaceutical compositions according to the present embodiments may be provided as unit dosage forms.

Means and methods for formulating the present pharmaceutical preparations are known to persons skilled in the art, and may be manufactured in a manner which is in itself known, for example, by means of conventional mixing, granulating, dissolving, lyophilizing or similar processes.

In the food additive of the invention, any non-toxic carrier acceptable for use in food can be mixed with a present heteropolysaccharide composition. The food product according to this invention is especially a functional food, a nutritional supplement, a nutrient, a pharmafood, a nutraceutical, a health food, a designer food or any food product. The functional food according to this invention can, for example be in form of biscuits, bread, cake, candy, fermented milk product or cereal.

It will be obvious to a person skilled in the art that, as the technology advances, the inventive concept can be implemented in various ways. The invention and its embodiments are not limited to the examples described below but may vary within the scope of the claims.

EXAMPLES

All animal experiments were conducted with the approval of the National Committee for Animal Experiments.

Example 1. Inhibition of Prostate Cancer Cell Proliferation by GGM-rich Heteropolysaccharide Compositions Effects of a purified (by precipitation in ethanol) GGM-rich hot-water extract derived from Norway spruce wood (as in example 2, method 1) on cell proliferation was tested in a prostate cancer cell line, namely LNCaP cell line, which is an androgen-sensitive human prostate adenocarcinoma cell line.

To this end, the cells were cultured in cell culture bottles in an incubator at 37° C. in the presence of 5% carbon dioxide using a culture medium recommended by the cell line provider (ATCC). 48 hours after plating, the GGM-rich extract was added in different concentrations (ranging from 1% to $1 \times 10^{-4}$% of the final cell medium) to the cells. For each concentration, six parallel wells were used. Two known compounds used in chemotherapy, namely Gemcitabine and Ara-C, were used as positive controls (100 nM).

After 3 or 5 days of incubation, WST-1-reagent (Roche) was used to measure the proliferation of the cells according to the manufacturer's instructions. This type of a proliferation assay is based on living cells' ability to reduce the WST-1 reagent to a yellow formazan compound, the amount of which is proportional to the proliferation rate and can be measured spectrophotometrically. Briefly, 10 μl of WST-1 was added into each well and the cells were incubated for 2 hours at 37° C. in the presence of carbon dioxide. After the incubation, absorbance at 450 nm was measured from each well using Wallac Victor2 multilabel counter.

Statistical analyses were performed using Sigmastat® software package. Comparisons were made using ANOVA, while Student-Newman-Keuls-Method was used as a post-hoc-test. All results are represented as average values and standard deviation. *=P<0.001 compared to PBS, =P<0.005 compared to PBS, *=P<0.05 compared to PBS.

The results showed that the GGM-rich softwood extract reduced cancer cell proliferation concentration-dependently (FIG. 1). Similar results were obtained using another prostate cancer cell line, namely PC-3 cell line, which is an androgen-independent cell line derived from a bone-metastasized prostatic cancer.

Example 2. In Vivo Effects of GGM-rich Heteropolysaccharide Compositions on LUT Symptoms and Pelvic Pain An in vivo model of chronic nonbacterial prostatitis/chronic pelvic pain syndrome (CP/CPPS) is an established tool to study prostatic inflammation and associated changes on voiding. Symptoms of prostatitis include genitourinary and/or pelvic pain associated with changes in urination, such as hesitancy, interrupted stream, weak stream, urgency and frequency. These symptoms can be experimentally modelled by hormonal exposure. Experimental studies have shown gradual development of prostatic inflammation within six weeks after combined testosterone and estradiol treatment of intact adult male rats. When using corresponding hormonal treatment for more than 13 weeks, animals develop more advanced inflammation resembling human chronic prostatic inflammation. Additionally, hormonal treatment induces obstructive voiding seen e.g. as decreased urinary flow rates, increased micturition times, and decreased voided volumes. Obstructive voiding is associated with prostatic glandular inflammation.

Effects of orally administered GGM-rich coniferous tree extracts were tested in the above animal model for hormone-induced voiding alterations associated with prostatic inflammation. The study was repeated two times individually to get a conformation of the results.

At the beginning of the study, male Wistar rats were implanted ed with testosterone (T) and estradiol ($E_2$) implants. Daily released hormone amount was 830 μg for T and 83 μg for $E_2$. The total hormonal exposure time was 18 weeks.

GGM-rich heteropolysaccharide products were extracted from Norway spruce by two different methods:

Extraction method 1: Spruce wood meal was extracted with water in a batch extractor (Accelerated Solvent Extractor) and purified by precipitation in aqueous ethanol yielding a heteropolysaccharide preparate with a molar mass in the range of 4000 to 20000, with an average Mw of 9200 Dalton. The product was composed mainly of galactoglucomannan (GGM) and smaller amounts of xylans and pectins. The carbohydrate composition determined by acid methanolysis and gas chromatography was:

Galactose 7%, glucose 15%, mannose 60%, i.e. total GGM 82%

Arabinose 1%, 4-O-methylglucuronic acid 2%, xylose 9%, i.e. total xylans 12%

Rhamnose 0.3%, galacturonic acid 3.5%, i.e. total pectins 4%

The product contained 0.6% acetyl groups, corresponding to an acetyl:mannose ratio of about 0.5.

Extraction method 2: Another preparate was produced by extraction in a flow-through extractor (Leppänen et al. 2011, ibid.) and further purified by precipitation in ethanol: water. This second preparate had an average molar mass of 8200 Dalton. Its carbohydrate composition was very similar to the first product.

Independent animal experiments were performed using both extracts. To this end, the extracts were dissolved in tap water as 2% solutions. The extract solutions were put into animal drinking bottles to which animals had free access. Tap water was given to the control group as a vehicle. Animals had free access to the vehicle or extract for 5 weeks (between study weeks 13 and 18). After the total hormone exposure for 18 weeks, urodynamical measurements were performed under anesthesia.

For urodynamical measurements, a catheter was inserted through the bladder apex into the lumen. The catheter was connected to an infusion pump and to a pressure transducer for bladder pressure measurements. For inducing voiding reflexes, physiological saline was infused into the bladder at an infusion rate of 10 ml/h. An ultrasonic flow probe connected to a flow meter was used for measurement of the flow rate from the distal part of urethra. Decrease in urine flow rates and micturition intervals and voided volumes, and increase in micturition time and bladder pressure was considered to be signs of obstructive voiding.

Figure 2:
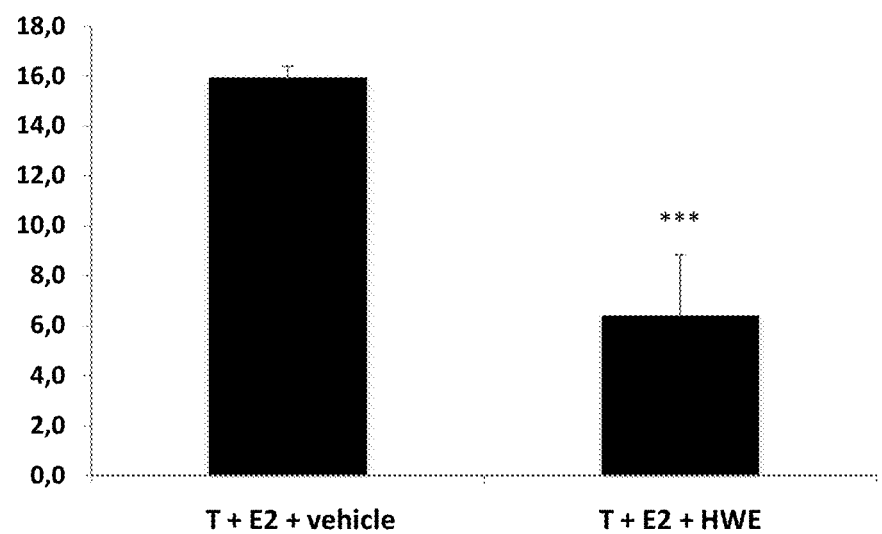
FIG. 2 shows basal bladder pressures (as $cmH_2O$) measured on male rats treated with either a vehicle or a softwood heteropolysaccharide extract.
Figure 3:
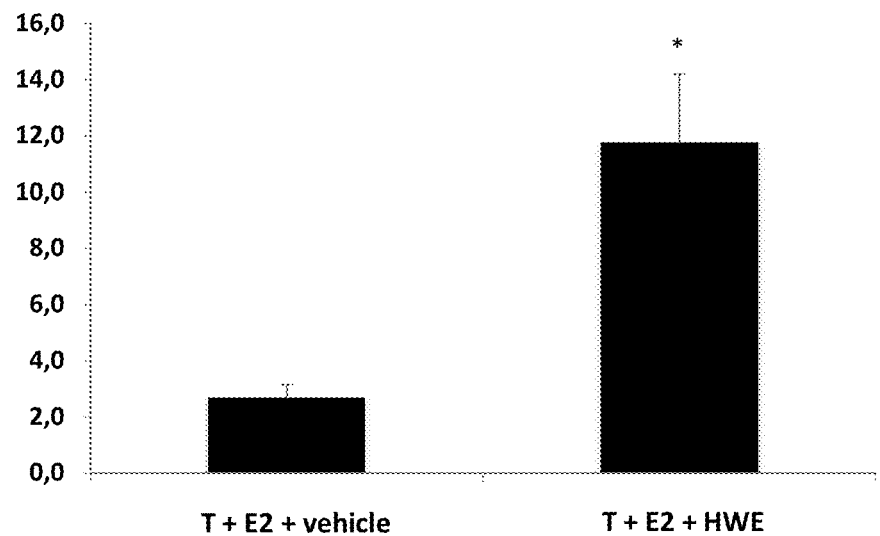
FIG. 3 shows a mean urine flow (as ml/min) measured on male rats treated with either a vehicle or a softwood heteropolysaccharide extract.
Figure 4:
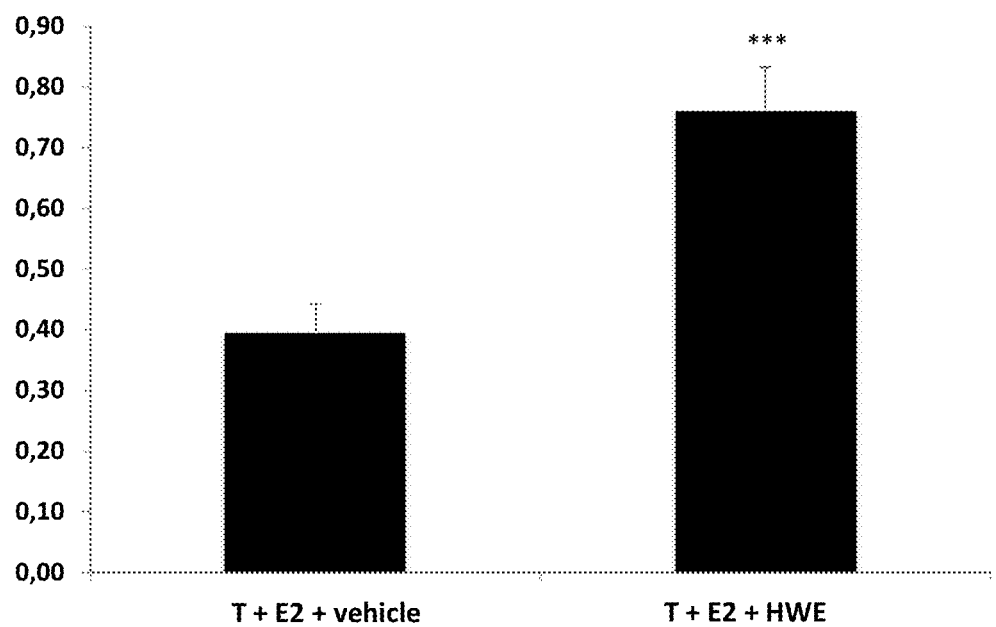
FIG. 4 shows voided volumes (as ml) measured on male rats treated with either a vehicle or a softwood heteropolysaccharide extract.

Both separately performed studies showed that the GGM-rich softwood extract had clear beneficial effects on obstructive voiding by improvingsigns of obstructive voiding, i.e. decreasing basal bladder pressure (FIG. 2), increasing urinary flow rates (FIG. 3) and increasing voided volumes (FIG. 4). Treatment with the extract also increased micturition intervals and decreased micturition times showing improvement of bladder function.

Figure 5:
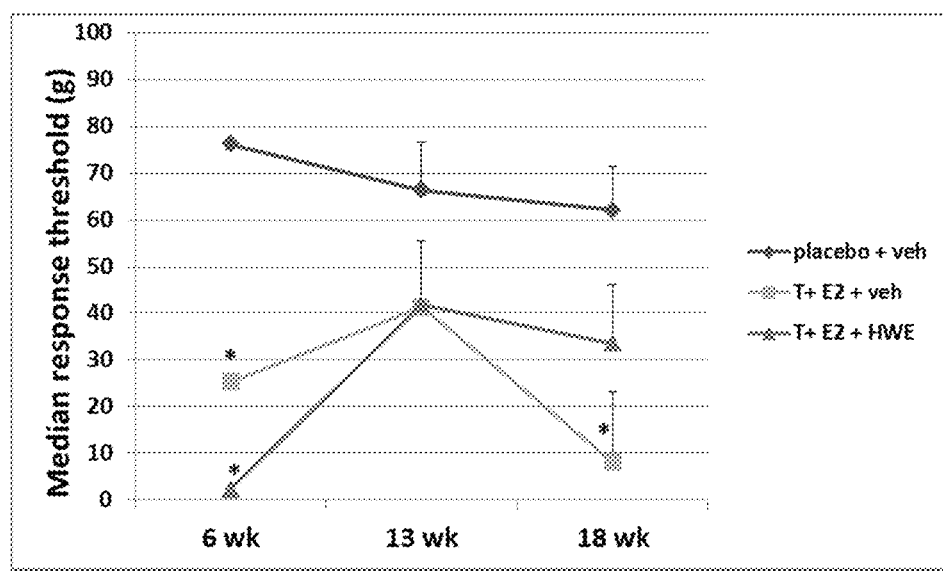
FIG. 5 shows abdominal pain assessment during the study, measured with von Frey filaments. The response threshold is the force as grams measured with von Frey filaments where animals respond to pain; the larger the value, the higher threshold the animals have to pain stimulus.

In addition to assessing signs of obstructive voiding, assessmentof abdominal pain was performed (FIG. 5). Pelvic pain assessment was measured from animals at three time points during the study by stimulating the abdominal area of the male rats with von Frey filaments. For comparison, pain stimulus was measured also from non-hormonally treated rats showing the basal response to the von Frey filaments. Results show that hormone treatment does increase pelvic pain resembling the clinical signs in patents with prostatic inflammation associated with pelvic pain. Results show that treatment with the extract reduces the feeling of pain relative to vehicle treated animals by increasing pain threshold.

Based on the results of two repeated studies described above it can be concluded that GGM-rich softwood extracts have clear beneficial effects on obstructive voiding and reduce abdominal pain occurring concomitantly with inflammation. Without being bound to any hypothesis, the mechanism of action is most probably based on direct effects on the function of lower urinary tract.

Example 3. Effects of GGM-rich Heteropolysaccharide Compositions on Prostate Cancer Incidence and Precancerous Changes Prostate samples obtained from studies described in Example 2, were assessed histologically for prostatic precancerous changes.

After fixing the prostate samples in 10% neutral formalin solution for 18-20 hours, the samples were moved to 70% ethanol for storage. Thereafter, the prostates were dehydrated with ethanol-xylen solutions and embedded into paraffin. From each prostate sample, sections were cut at 100-200 μm distances. Thereafter, the sections were stained by hematoxylin and eosin (H&E). Histopathological assessment was done from the H&E stained prostate sections of each animal. From each block two sections were examined for the cancer (incidence and area in $mm^2$). For each animal average values were calculated from values obtained from these two levels.

Figure 6:
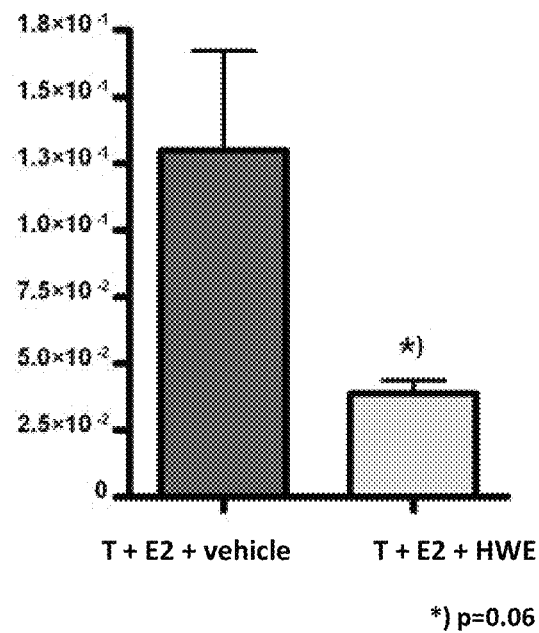
FIG. 6 illustrates the total cancer area (as $mm^2$) measured from histological prostate sections obtained from male rats treated either with a vehicle or a softwood heteropolysaccharide extract.

The results showed that the softwood extracts tested clearly decreased the total cancer area measured from the histological sections (FIG. 6). Furthermore, the hormone treatment induced prostate cancer in about 57% of the control group animals, while in the extract-treated animal group, the prostate cancer incidence decreased to about 38%.

The invention claimed is:

1. A method of treating at least one urologic disease in a human or animal subject in need thereof by administering an effective amount of a ligneous plant-derived composition comprising heteropolysaccharides to said subject, wherein galactoglucomannans (GGMs) constitute at least 50% of the total carbohydrate content of the composition, wherein the disease is interstitial cystitis/bladder pain syndrome, hemorrhagic cystitis, chronic nonbacterial prostatitis/chronic pelvic pain syndrome, benign prostate hyperplasia, or renal cell carcinoma.

2. The method according to claim 1, wherein said composition comprises hemicellulose and/or pectic compounds.

3. The method according to claim 1, wherein said composition is in a form of a water-extract.

4. The method according to claim 1, wherein said composition is in a form of an isolated carbohydrate composition.

5. The method according to claim 1, wherein GGMs constitute at least 80% of the total carbohydrate content of the composition.

6. The method according to claim 1, wherein said composition comprises oligosaccharides with two to ten sugar units selected from the group consisting of mannose, glucose, galactose and xylose sugar units.

7. The method according to claim 1, wherein said disease shows at least one symptom is-selected from the group consisting of increased daytime urinary frequency, nocturia, urinary incontinence, urinary urgency, intermitted urine stream, slow urine stream, split-ting or spraying of the urine stream, prolonged micturition hesitancy, straining and terminal dribble, incomplete bladder emptying, post-micturition dribble, abdominal pain, pelvic pain, genitourinary pain, bladder pain, urethral pain, vulval pain, vaginal pain, scrotal pain, and perineal pain.

8. A method of treating at least one urologic symptom or disease in a human or animal subject in need thereof by administering an effective amount of a ligneous plant-derived composition comprising heteropolysaccharides to said subject, wherein galactoglucomannans (GGMs) constitute at least 50% of the total carbohydrate content of the composition, wherein the disease is hemorrhagic cystitis.

9. The method according to claim 8, wherein said composition is in a form of a water-extract.

10. The method according to claim 8, wherein GGMs constitute at least 80% of the total carbohydrate content of the composition.

11. A method of treating at least one urologic symptom or disease in a human or animal subject in need thereof by administering an effective amount of a ligneous plant-derived composition comprising heteropolysaccharides to said subject, wherein galactoglucomannans (GGMs) constitute at least 50% of the total carbohydrate content of the composition, wherein the disease is chronic nonbacterial prostatitis/chronic pelvic pain syndrome.

12. The method according to claim 11, wherein said composition is in a form of a water-extract.

13. The method according to claim 11, wherein GGMs constitute at least 80% of the total carbohydrate content of the composition.

14. A method of treating at least one urologic symptom or disease in a human or animal subject in need thereof by administering an effective amount of a ligneous plant-derived composition comprising heteropolysaccharides to said subject, wherein galactoglucomannans (GGMs) constitute at least 50% of the total carbohydrate content of the composition, wherein the disease is benign prostate hyperplasia.

15. The method according to claim 14, wherein said composition is in a form of a water-extract.

16. The method according to claim 14, wherein GGMs constitute at least 80% of the total carbohydrate content of the composition.

17. A method of treating at least one urologic symptom or disease in a human or animal subject in need thereof by administering an effective amount of a ligneous plant-derived composition comprising heteropolysaccharides to said subject, wherein galactoglucomannans (GGMs) constitute at least 50% of the total carbohydrate content of the composition, wherein the disease is renal cell carcinoma.

18. The method according to claim 17, wherein said composition is in a form of a water-extract.

19. The method according to claim 17, wherein GGMs constitute at least 80% of the total carbohydrate content of the composition.

* * * * *